United States Patent [19]

Pelta

[11] Patent Number: 4,702,230

[45] Date of Patent: Oct. 27, 1987

[54] ADAPTER FOR SURGICAL RETRACTOR

[75] Inventor: Samuel Pelta, Philadelphia, Pa.

[73] Assignee: Pilling Co., Fort Washington, Pa.

[21] Appl. No.: 938,880

[22] Filed: Dec. 8, 1986

[51] Int. Cl.[4] ............................................ A61B 17/02
[52] U.S. Cl. .................................... 128/20; 403/393;
403/362
[58] Field of Search ....................... 403/362, 393, 377;
128/203, 12, 17; 433/140, 155, 161, 7; 248/298;
24/37, 105

[56] References Cited

U.S. PATENT DOCUMENTS

| 2,623,517 | 12/1952 | Barlow et al. | 128/20 |
| 2,680,923 | 6/1954 | Hyland | 403/393 |
| 3,040,739 | 6/1962 | Grieshaber | 128/20 |
| 3,384,077 | 5/1968 | Gauthier | 128/20 |
| 4,099,521 | 7/1978 | Nestor et al. | 128/20 |
| 4,467,791 | 8/1984 | Cabrera et al. | 128/20 |

FOREIGN PATENT DOCUMENTS

| 1019217 | 1/1953 | France | 128/20 |
| 168216 | 9/1921 | United Kingdom | 128/20 |

OTHER PUBLICATIONS

Pilling Bulletin 99-3004 Entitled "Modified Carpentier Type Sternal/Atrial Retractor", Sep. 1984.
Delacroix Chevalier Advertisement Entitled "Ecarteur Thoracique".
Catalog Entitled "Cardiovascular Thoracic, General Surgical Pilling Instruments", 1979, p. 56.

Primary Examiner—Richard C. Pinkham
Assistant Examiner—Mark S. Graham
Attorney, Agent, or Firm—Howson and Howson

[57] ABSTRACT

An adapter for attaching atrial blades to a sternal spreader comprises an elongated bar having blade attaching means on an oblique surface, and having a heel, hook and adjusting screw on its bottom surface. The heel and the head of the adjusting screw are engageable with the upper surface of a spreader arm, and the hook is engageable with the lower surface thereof. The screw has a wheel formed on it, which is located between the bar and the spreader arm. When this wheel is turned to cause the screw to extend, the hook and heel of the bar and the head of the screw are pressed against the spreader arm, causing the adapter to be firmly secured to the spreader.

11 Claims, 6 Drawing Figures

ADAPTER FOR SURGICAL RETRACTOR

BRIEF SUMMARY OF THE INVENTION

This invention relates to surgical retractors and particularly to an adapter for securing an auxiliary blade to a surgical spreading retractor. The invention has particular utility in mitral valve surgery, and will be described with reference to an adapter for securing atrial retractors to a conventional sternal spreader.

One form of retractor mechanism which has been used for a number of years in mitral valve repair or replacement is known as a Carpentier retractor. The Carpentier retractor is a specialized form of sternal spreader in which atrial retraction blades are removably attached to retaining projections on one of the spreader arms. The spreader comprises a pair of parallel arms. One of these arms is fixed to one end of a toothed rack, and the other is slidable along the rack. The spacing between the arms is adjusted by a crank-operated pinion. Each arm has a single sternal spreading blade. In addition, the movable arm has an oblique surface with a series of projections for retaining specially designed atrial blades. Each of the special blades is in the form of a strip of metal having a straight intermediate portion and curved portions at both ends. The straight portion has a series of slits, each of which is engageable with a retaining projection on the movable arm so that the blade can be placed in any selected one of a plurality of positions relative to the movable arm. A typical blade has ten such slots. The curved portion formed at one end of the blade is used for atrial retraction, and the curved portion at the opposite end of the blade is grasped by the surgeon when the blade is being attached to or removed from a retaining projection on the retractor arm.

The Carpentier retractor just described is a specialized retractor having a specific sternal spreading blade configuration. Several forms of sternal spreading retractors are available which have blade configurations which are in at least some instances more desirable than those of the Carpentier retractor. However, these general purpose sternal spreading retractors lack the retaining projections necessary to hold the slotted atrial blades. Adding such retaining projections to existing retractors or providing them on new sternal spreading retractors of various sizes and designs would be impractical.

It is accordingly an object of the invention to enable a conventional sternal spreading retractor to be used for mitral valve surgery by providing an adapter for securing slotted atrial blades to one of the arms of the spreader. More generally, it is an object of the invention to provide a form of adapter which can be conveniently used to secure various auxiliary devices to a surgical spreading retractor or similar instrument.

It is also an object of the invention to allow the surgeon, who desires to perform mitral valve surgery with slotted atrial blades, to use the form of sternal spreading retractor which he prefers, rather than to limit him to a specific form of retractor having a particular spreader blade configuration.

It is also an object of the invention to provide a very secure attachment of an adapter to an arm of a spreading retractor, and to minimize obstruction of the surgical field by adapter parts.

Still another object of the invention is to provide an adapter which can be conveniently secured to either arm of a conventional spreading retractor so that the rack thereof can be positioned toward the patient's head or toward the patient's feet, as desired by the surgeon.

In accordance with this invention, an adapter is secured to a conventional spreading retractor. The conventional retractor comprises a pair of rigid arms in spaced, substantially parallel relationship to each other, each arm having first blade means supported thereon, the first blade means being typically sternal spreading blades. The retractor also comprises means connected to the arms for holding them in substantially parallel relationship and for adjusting the spacing of the arms. The adapter is used to secure at least one auxiliary blade to one of the arms. The adapter is removably supported on one of the arms and comprises an elongated bar extending substantially lengthwise along the arm on one side thereof. Means are provided on the bar for holding the auxiliary blade. Hook means are rigidly fixed to the bar at an intermediate position along its length. The hook means comprises a first portion engaged with the opposite side of the arm and an interconnecting portion connecting the first portion of the hook means to the bar. Heel means are located substantially at one of the bar and engaged with said one side of the arm. Screw means, located on the side of the hook means remote from the heel, are threaded into the bar and extend from the bar toward said one side of the arm. The screw means has a head engaged with said one side of the arm and a wheel formed thereon, the wheel being located between the bar and the arm, and extending radially beyond the bar in at least one direction so that it can be grasped and rotated manually. The screw is tightened so that its head and the heal means of the bar bear tightly against said one side of the arm and the first portion of the hook means bears tightly against the opposite side of the arm so that the adapter is firmly secured to the arm. The adapter is easily secured to and removed from the spreader arm, can be used with a wide variety of spreaders, and takes up very little space.

Further objects, advantages and details of the invention will be apparent from the following detailed description when read in conjunction with the drawings.

DETAILED DESCRIPTION

Figure 1:
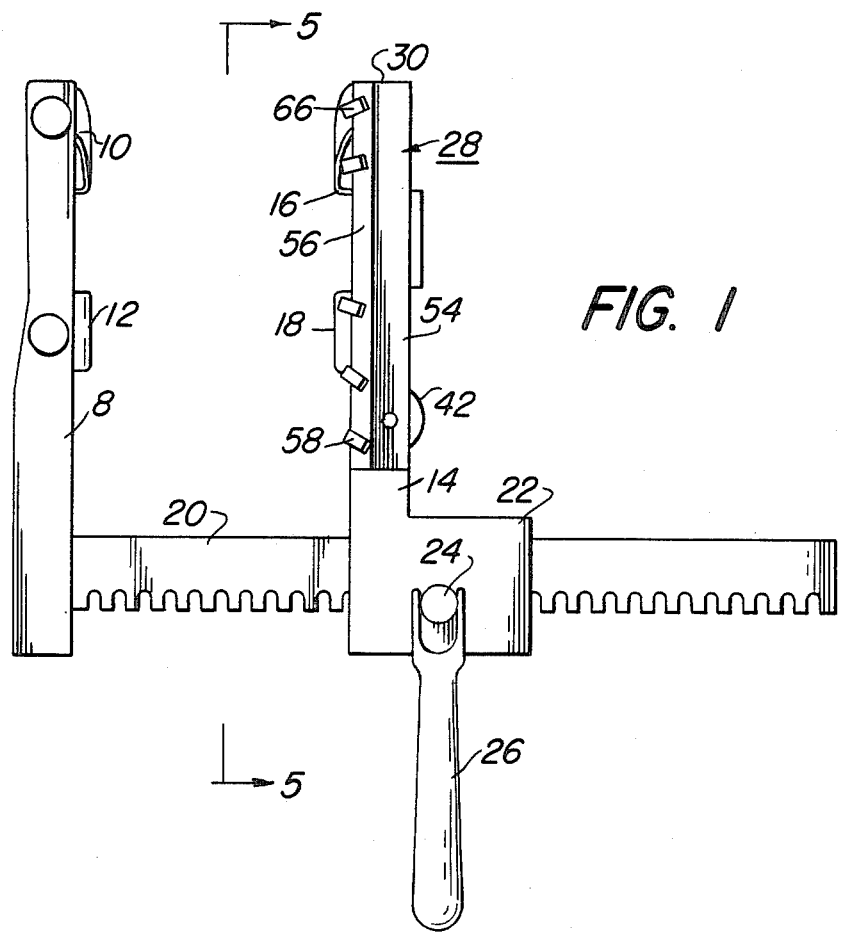
FIG. 1 is a top plan view of a conventional spreading retractor with the adapter mounted on one arm thereof.

FIG. 1 shows a sternal spreading retractor comprising an elongated arm 8 having a pair of swivelling blades 10 and 12, and an elongated arm 14 having a similar pair of swivelling blades 16 and 18. These two arms are maintained in parallel relationship to each other by a rack 20. Arm 8 is fixed at one end of the rack, and arm 14 is an extension of a slide 22 which is movable along the rack by a pinion (not shown) on shaft 24. The shaft is rotatable by crank 26.

The particular sternal spreading retractor shown in FIG. 1 is known as a Favaloro-Morse sternal spreader. Numerous similar sternal spreading retractors are available, and the adapter of the invention is applicable to many of them.

Figure 2:
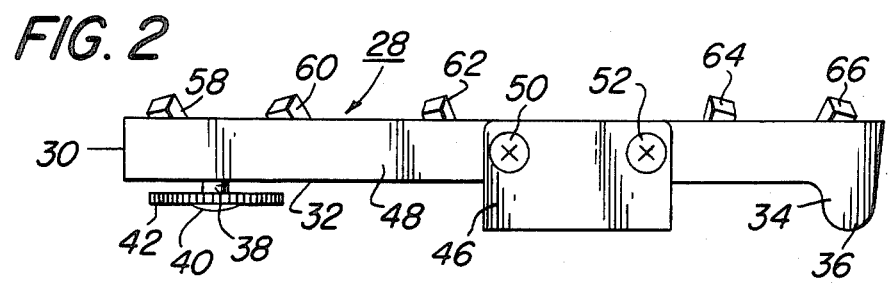
FIG. 2 is a side elevation of the adapter, as viewed from the right-hand side of FIG. 1.
Figure 3:
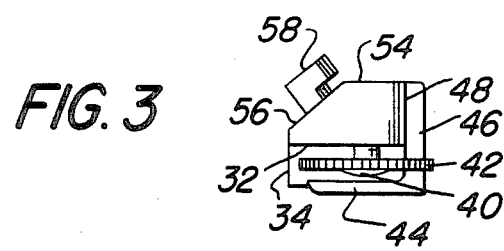
FIG. 3 is an end elevation of the adapter as viewed from the left-hand side of FIG. 2.

Referring to FIGS. 1, 2 and 3, the adapter, generally indicated at 28, comprises an elongated stainless steel bar 30 situated on top of spreader arm 14 and extending generally in parallel to the spreader arm. The bar preferably has a planar bottom face 32 with a heel 34 projecting downwardly therefrom substantially at one end of the bar, as shown in FIGS. 2 and 3. Heel 34 has a rounded cylindrical surface 36 extending transverse to the direction of elongation of the bar. More specifically, straight lines in the rounded cylindrical surface of the heel extend substantially perpendicular to an imaginary plane intersecting the bottom face of the bar perpendicularly along a centerline parallel to the direction of elongation of the bar.

Near the opposite end of the bar, a screw 38 is threaded into bottom face 32 so that it extends generally perpendicular to the bottom face and downwardly therefrom. The screw has a rounded head 40 which is preferably substantially spherical in shape. The screw is also formed with a wheel 42 located just above the head. Wheel 42 has a knurled edge and preferably extends horizontally beyond the side boundaries of the bar at least in one direction, as shown in FIGS. 1 and 3 so that it is visible from above and can be easily rotated by a surgeon to adjust the distance between screw head 40 and bottom face 32 of the bar.

At an intermediate portion of the bar there is secured a hook comprising a bottom portion 44 and a connecting portion 46. The connecting portion is fastened to side wall 48 of the bar by machine screw 50 and 52 so that the connecting portion is well offset from the centerline of the bottom of the bar to provide a clear space between the bottom of the bar and portion 44 of the hook. When the adapter is secured to arm 14 of the sternal spreading retractor, arm 14 extends underneath head 40 of screw 38, over portion 44 of the hook, and underneath cylindrical surface 36 of heel 34.

As seen in FIGS. 1, 2 and 3, the upper face of the bar comprises a horizontal surface 54 and an oblique surface 56. The sloping surface lies in a plane which intersects the plane of bottom face 32 along a line of intersection which extends substantially parallel to the direction of elongation of the bar. A series of retaining projections, 58, 60, 62, 64 and 66 are provided on the oblique surface for engaging slots in atrial blades. These retaining projections are of a configuration similar to those in the well-known Carpentier retractor.

Figure 5:
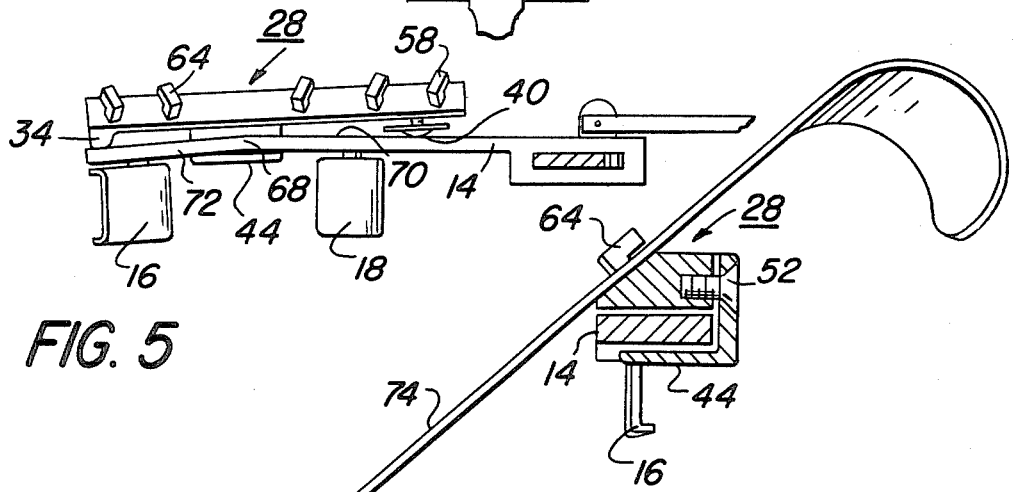
FIG. 5 is a vertical section taken on plane 5—5 indicated in FIG. 1.

As shown in FIG. 5, arm 14 of the sternal spreading retractor is bent at 68 so that top surface 70 is convex. This bend allows the spreader arm to conform to the shape of the sternum. The positions of heel 34, portion 44 of the hook, and head 40 of the screw are such as to accommodate the bend in the spreader arm. To attach adapter 28 to the spreader arm, portion 44 of the hook is placed underneath bend 68, and with heel 34 and screw head 40 both in contact with upper surface 70 of arm 14, the screw is turned by rotation of its wheel until portion 44 of the hook comes into contact with bottom surface 72 of arm 14. When the screw is tightened, the adapter is firmly secured to the retractor arm.

Figure 4:
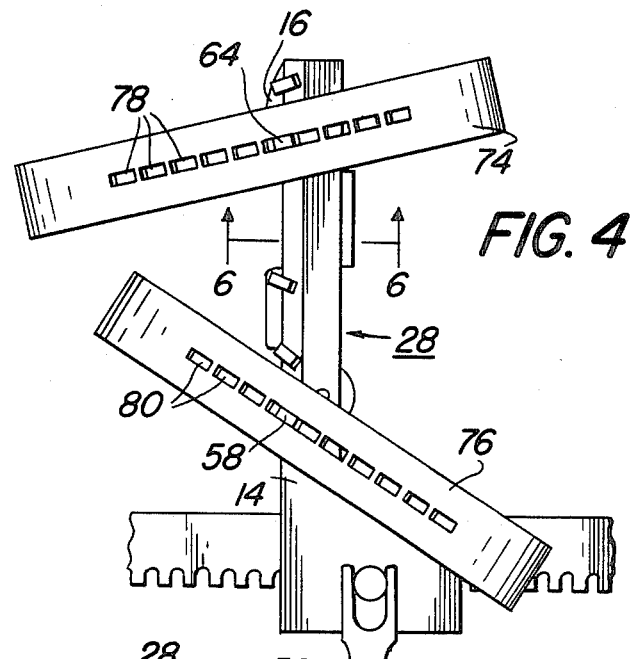
FIG. 4 is a fragmentary top plan view showing an adapter on a spreader arm, with two atrial blades attached to it.
Figure 6:
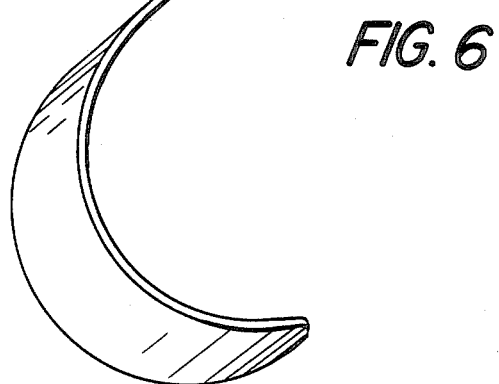
FIG. 6 is a vertical section taken on plane 6—6 indicated in FIG. 4.

Atrial blades 74 and 76 can be attached to selected retaining projections on the retractor. As shown in FIG. 4, blade 74 is held on retaining projection 64 and blade 76 is held on retaining projection 58. The manner in which blade 74 is held on retaining projection 64 is shown in more detail in FIG. 6.

As will be apparent from FIG. 5, the heel, hook and tightening screw of the adapter are positioned unobtrusively, and do not interfere in any way with the surgery being performed. The use of the heel, hook and adjusting screw allows the adapter to be positioned at any location in a range of locations along the retractor arm. No modifications to the spreading retractor are required. While the adapter is shown attached to the movable arm of the spreading retractor, it can be easily attached to the fixed arm if desired. If the retractor is attached to the fixed arm, the heel would be located adjacent to the rack, while the screw would be located adjacent to the remote end of the arm. The adapter, while shown attached to one arm of a Favaloro-Morse sternal spreader, can be used with various other forms of retractors, and with retractors of various sizes.

The adapter can be modified in numerous respects, for example in the configuration of the retaining elements or in the configurations of the heel, hook and tightening screw. Numerous other modifications can be made to the adapter without departing from the scope of the invention as defined in the following claims.

I claim:

1. An adapter for securing an auxiliary blade to a surgical spreading retractor comprising:

an elongated bar having a top face and a bottom face;

means on the top face of said bar for holding auxiliary retractor blade means;

hook means rigidly fixed to the bar at an intermediate position along the length of the bar, said hook means having a first portion located underneath the bottom face of the bar and spaced therefrom, and an interconnecting portion extending from said first portion to the bar and connected to the bar at a location laterally offset from a centerline extending lengthwise along the bottom face of the bar;

heel means located substantially at one end of the bar; and screw means located on the side of the hook means remote from the heel means and threaded into the bottom face of the bar, said screw means having a head and a wheel formed thereon, said wheel being located between the head and the arm and extending radially beyond the bar in at least one direction.

2. An adapter according to claim 1 in which the heel means projects downwardly from said bottom face of the bar substantially at said one end thereof.

3. An adapter according to claim 2 in which said heel comprises a substantially cylindrical outer surface extending in a direction transverse to the direction of elongation of the bar.

4. An adapter according to claim 1 in which said head of the screw means is a rounded convex head.

5. An adapter according to claim 1 in which at least a major portion of the bottom face of the bar is substantially planar, in which the top face of the bar comprises a substantially planar surface which is oblique with respect to the planar portion of the bottom face and the plane of said oblique surface intersects the plane of the bottom face along an intersection line substantially parallel to the direction of elongation of the bar, and in which the means for holding auxiliary retractor blade means comprises a plurality of retainer projections located on said oblique surface.

6. A surgical retractor comprising:
a pair of rigid arms in spaced, substantially parallel relationship to each other, each arm having first blade means supported thereon;
means connected to said arms for holding the same in said substantially parallel relationship and for adjusting the spacing of said arms; and
at least one auxiliary blade;
wherein the improvement comprises an adapter removably supported on one of said arms, said adapter comprising an elongated bar extending substantially lengthwise along said one arm on one side thereof, means on said bar holding said auxiliary blade, hook means rigidly fixed to the bar at an intermediate position along the length of the bar, said hook means having a first portion engaged with the opposite side of said one arm and an interconnecting portion connecting the first portion to the bar, heel means located substantially at one end of the bar and engaged with said one side of the arm, and screw means threaded into the bar at a location on the side of the hook means remote from the heal means, said screw means extending from the bar toward said one side of the arm, said screw means having a head engaged with said one side of the arm and a wheel formed thereon, said wheel being located between the bar and the arm and extending radially beyond the bar in at least one direction whereby it can be grasped and rotated manually, said screw being tightened so that the head thereof and said heel means bear tightly against said one side of the arm, and said first portion of the hook means bears tightly against said opposite side of the arm, whereby the adapter is firmly secured to said arm.

7. A surgical retractor according to claim 6 in which said one of said arms is bent at a location between said heel and the head of said screw means in a direction such that said one side thereof presents a convex surface to the adapter.

8. A surgical retractor according to claim 7 in which said heel means projects from said one end of the bar toward said one side of the arm, and said one end of the bar is held by said heel means in spaced relationship with said one side of the arm.

9. A surgical retractor according to claim 8 in which said heel means comprises a substantially cylindrical outer surface extending in a direction transverse to the direction of elongation of said bar and contacting said one side of the arm along a line of contact parallel to said transverse direction.

10. A surgical retractor according to claim 6 in which said head of the screw means is a rounded convex head.

11. A surgical retractor according to claim 6 in which said bar has a face opposed to said one side of the arm, at least a portion of said face being substantially planar, in which the side of the bar opposite to said face comprises a substantially planar surface which is oblique with respect to said planar portion of said face and the plane of said oblique surface intersects the plane of said face along an intersection line substantially parallel to the direction of elongation of the bar, and in which the means on said bar holding said auxiliary blade comprises a retainer projection located on said oblique surface.

* * * * *